United States Patent
Procter et al.

(10) Patent No.: US 7,338,979 B2
(45) Date of Patent: Mar. 4, 2008

(54) DEPIGMENTATION AGENTS

(75) Inventors: Martin James Procter, Bicester (GB); William Thomas Gattrell, Bicester (GB)

(73) Assignee: Warner-Lambert Company, Ann Arbor, MI (US)

( * ) Notice: Subject to any disclaimer, the term of this patent is extended or adjusted under 35 U.S.C. 154(b) by 530 days.

(21) Appl. No.: 10/766,078

(22) Filed: Jan. 28, 2004

(65) Prior Publication Data

US 2004/0186186 A1  Sep. 23, 2004

Related U.S. Application Data

(60) Provisional application No. 60/446,665, filed on Feb. 11, 2003.

(51) Int. Cl.
*A61K 31/045* (2006.01)
*A61K 31/05* (2006.01)

(52) U.S. Cl. .................. 514/729; 514/730; 514/731

(58) Field of Classification Search ............... 514/719, 514/729, 730, 731
See application file for complete search history.

(56) References Cited

U.S. PATENT DOCUMENTS 6,132,740 A * 10/2000 Hu .............................. 424/401

2004/0235963 A1 * 11/2004 Gattrell ........................ 514/719

FOREIGN PATENT DOCUMENTS

EP  1134207 A1  9/2001

OTHER PUBLICATIONS

Yusupov et al., "Reaction of resorcinol and its methyl esters with cyclopentene and cyclohexene", Uzbek Chemical Journal, vol. 14, No. 5, 1970, pp. 66-69 (Chem. Abstract and English translation attached).
Ardurasuleva et al., "Cyclopentylation of resorcinol and its esters", Uzbek Chemical Journal, vol. 12, No. 5, 1968, pp. 37-41 (Chem. Abstract and English translation attached).
Yusupov et al., "Cycloalkylation of resorcinol and its esters", Uzbek SSR Academy of Sciences, vol. 27, No. 6, 1970, pp. 38-39 (Chem. Abstract and English translation attached).
Baek, "A Simple One-Step Alkylation of Orcinol Derivatives", Bull. Korean Chem. Soc., vol. 9, No. 2, 1988, pp. 71-77.

* cited by examiner

*Primary Examiner*—Alton Pryor
(74) *Attorney, Agent, or Firm*—Gregg C. Benson; J. Michael Dixon

(57) ABSTRACT

The present invention is directed to 4-cyclopentyl resorcinol monohydrate, its Form I polymorph, formulations containing at least one of these compounds, and their use to lighten skin.

9 Claims, 3 Drawing Sheets

DEPIGMENTATION AGENTS

CROSS-REFERENCE TO RELATED APPLICATIONS

This application claims the benefit of priority to U.S. Provisional Patent Application Ser. No. 60/446,665 filed Feb. 11, 2003.

FIELD OF THE INVENTION

The present invention is directed to 4-cyclopentyl resorcinol monohydrate and its Form I polymorph.

BACKGROUND OF THE INVENTION

In humans, skin color arises from a complex series of cellular processes that are carried out within a group of cells known as melanocytes. Melanocytes are located in the lower part of the epidermis and their function is to synthesize a pigment, melanin, which protects the body from the damaging effects of ultraviolet radiation.

The mechanism by which skin pigmentation is formed, melanogenesis, involves the following main steps: Tyrosine→L-Dopa→Dopaquinone Dopachrome→Melanin. The first two reactions in this series are catalyzed by the enzyme, tyrosinase. The activity of tyrosinase is promoted by the action of α-melanocyte stimulating hormone and UV rays.

Typically, melanogenesis leads to a darker skin tone (i.e. a tan). However, melanogenesis can lead to undesirable pigmentation patterns as well. Examples of such undesirable pigmentation include age spots, liver spots, melasma, hyperpigmentation, etc. This has lead to research to find compounds that will inhibit melanogenesis. One of the targets of this research is tyrosinase, the enzyme which catalyses the initial steps in the generation of melanin.

U.S. Pat. No. 6,132,740 discloses a class of tyrosinase inhibitors. These compounds are 4-cycloalkyl resorcinols. One compound disclosed in the '740 patent is 4-cyclopentyl resorcinol. Example 2 of the '740 patent illustrates the preparation of 4-cyclopentyl resorcinol. The synthesis described in Example 2 can lead to the production of an oil. While this oil is a potent tyrosinase inhibitor, it may not be readily produced in the quantities required to support clinical development.

The synthesis of example 2 generates substantial quantities of various positional isomers of 4-cyclopentyl resorcinol. Examples of such isomers include 2-cyclopentyl resorcinol, 4,6-dicyclopentyl resorcinol, 2,4-dicyclopentylresorcinol, etc. It is difficult to separate the 4-cyclopentyl resorcinol from its positional isomers, especially when all of the compounds are present as oils. Thus, a need exists in the art for solid forms of 4-cyclopentyl resorcinol that may be produced more readily than the anhydrate of the prior art.

SUMMARY OF THE INVENTION

In accordance with the present invention, a new solid form of 4-cyclopentyl resorcinol has been discovered. The solid form is 4-cyclopentyl resorcinol monohydrate. 4-Cyclopentyl resorcinol monohydrate may be represented by the following formula:

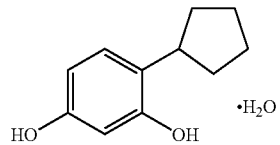

Formula 1

A further aspect of the invention is directed to a specific crystalline polymorph of 4-cyclopentyl resorcinol monohydrate. This polymorph is referred to as the Form I polymorph. It has a characteristic powder X-ray diffraction pattern that is described infra (XRPD). The structure of a single crystal of the Form I polymorph has also been determined and is reported infra.

The monohydrate of 4-cyclopentyl resorcinol, and its Form I polymorph, may be used to lighten skin (i.e. as a depigmentation agent). In a more specific embodiment, the compound is incorporated into a topical dosage form, which the patient may apply directly to the area of the skin requiring lightening.

In a further embodiment, the invention is directed to an article of manufacture containing either the monohydrate, or its Form I polymorph, packaged for retail distribution, in association with instructions advising the consumer how to use the product to lighten skin.

DETAILED DESCRIPTION OF THE INVENTION

A. Methods of Characterization

1) Experimental X-Ray Powder Diffraction

Figure 3:
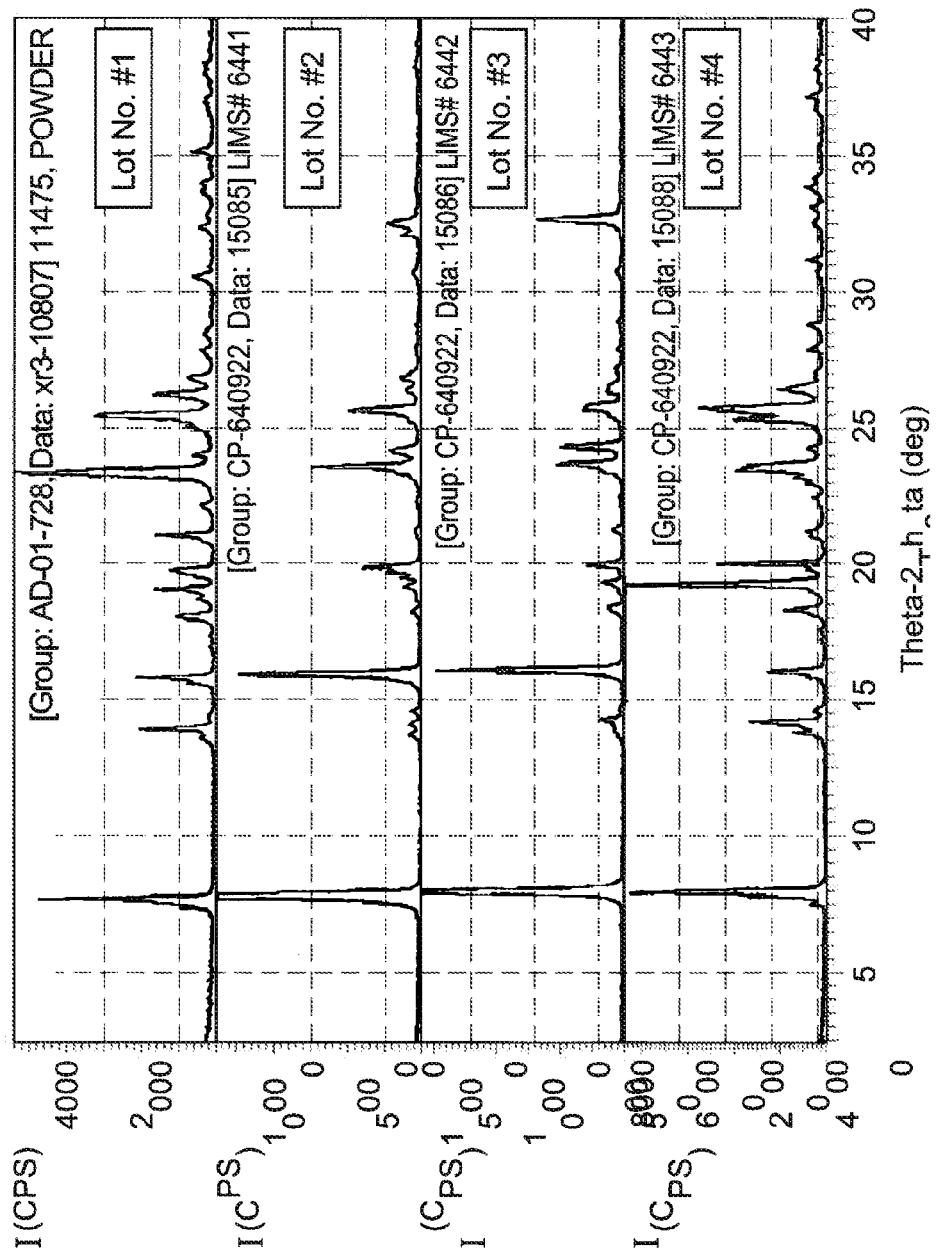
FIG. 3 shows the X-ray powder diffraction from 4 different lots of the Form I polymorph.

Those X-ray powder diffraction (XPRD) analyses depicted in FIG. 3 for lot numbers 2, 3, and 4 were carried out utilizing a Shimadzu XRD-6000 X-ray powder diffractometer using Cu $K_\alpha$ radiation. The instrument was equipped with a fine focus X-ray tube. The tube voltage and amperage were set to 40 kV and 40 mA, respectively. The divergence and scattering slits were set at 1° and the receiving slit was set at 0.15 mm. Diffracted radiation was detected by a NaI scintillation detector. A theta-two theta continuous scan at 3°/min (0.4 sec/0.02° step) from 2.5 to 40 °2θ was used. A silicon standard was analyzed to check the instrument alignment. Data were collected and analyzed using Shimadzu XRD-6000 v. 4.1 software. Samples were prepared for analysis by placing them in a silicon sample holder and leveling with a frosted glass slide.

Figure 1:
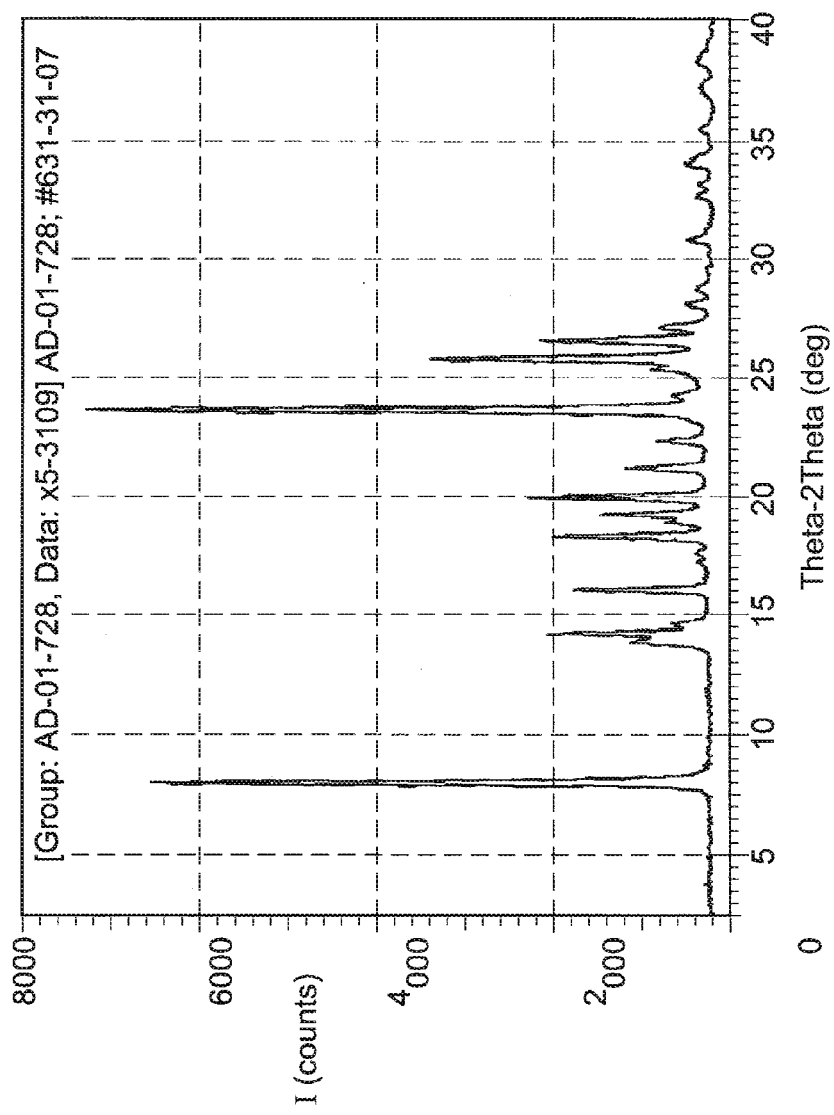
FIG. 1 depicts the X-ray powder diffraction pattern for the Form I polymorph, on a scale of 2.5 °2θ to 40 °2θ.
Figure 2:
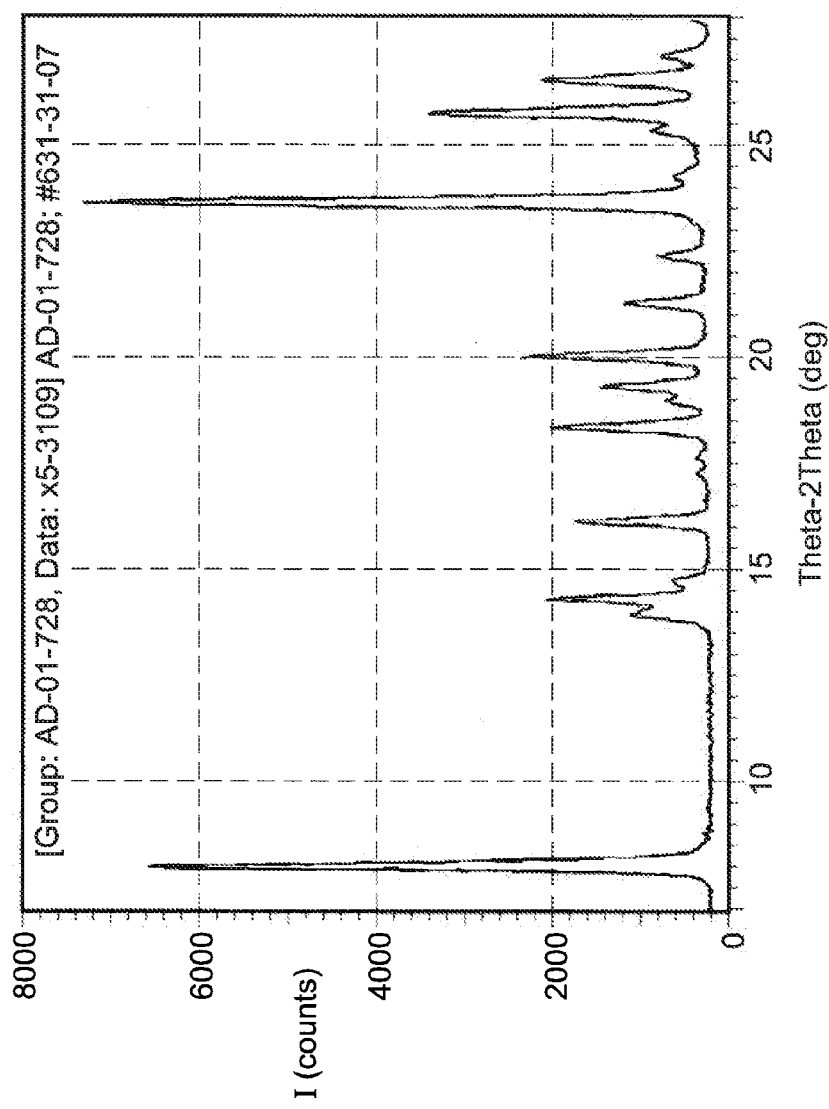
FIG. 2 shows the X-ray powder diffraction pattern for the Form I polymorph depicted on a condensed scale of 7 °2θ to 28 °2θ.

The X-ray powder diffraction (XPRD) analysis depicted in FIGS. 1, 2, and FIG. 3, (lot #1), was carried out using a Inel XRG-3000 diffractometer equipped with a curved position-sensitive detector, using Cu $K_\alpha$ radiation. Data was collected in real time over a two theta range of 120° at a resolution of 0.03°. The tube voltage and amperage were 40 kV and 30 mA, respectively. The sample was packed in an aluminum holder with a silicon insert and analyzed. A silicon standard was analyzed each day to check for instrument alignment. Data were collected using INEL Winplot v. 3.11 software and analyzed using Shimadzu XRD-6000 v. 4.1 software.

As is readily apparent to one skilled in the art, the results of any X-ray powder diffraction may vary. This variance can be due to test sample preparation, the particular model of X-ray diffractometer used, the operator's technique, etc. The term "approximately" if used in defining a position of a characteristic peak in an X-ray powder diffraction pattern is defined as the stated 2θ value±0.2 °2θ.

2) X-ray Single Crystal Structure Determination

A single crystal of Form I was mounted in a random orientation. Preliminary examination and data collection were performed with Mo $K_\alpha$ radiation on a Bruker SAMRT IK CCD diffractometer, available from Bruker AXS, Inc., Madison, Wis. Cell constants and an orientation matrix for data collection were obtained from least-squares refinement using the setting angles of 6145 reflections in the range 3°<θ<28°. The structure was solved by direct methods. The structure was refined by full-matrix least-squares on $F^2$. The crystal structure was determined at 160 K, solved in space group $P2_1/c$ and refined to a final R of $0.04(F^2>2\sigma)$.

B. 4-Cyclopentyl Resorcinol Monohydrate

As noted above, a new form of 4-cyclopentyl resorcinol has been discovered. This new form is the monohydrate of 4-cyclopentyl resorcinol. This substance may be represented by the following formula:

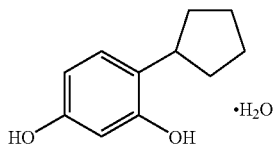

The term "monohydrate" is typically used to describe a substance in which one molecule of water associates with one molecule of a given compound (i.e. a 1:1 molar ratio). As used in this application, the term "monohydrate" should not be considered to have such a limited meaning. The inventors have discovered that the molar ratio of water to 4-cyclopentyl resorcinol can vary. As used in this application, the term "4-cyclopentyl resorcinol monohydrate" refers to a substance which contains from about 0.7 moles of water to about 1.4 moles of water for every mole of 4-cyclopentyl resorcinol. In a more specific embodiment, the monohydrate has about 0.8 to about 1.2 moles of water for every mole of 4-cyclopentyl resorcinol. In a more specific embodiment, the monohydrate has about 0.9 to about 1.2 moles of water for every mole of 4-cyclopentyl resorcinol.

This new form posses a number of advantages over the form of the prior art. One of the primary advantages is the simplicity of separating the 4-cyclopentyl resorcinol from the positional isomers described supra, such as 2-cyclopentyl resorcinol, 4,6-dicyclopentyl resorcinol, 2,4-dicyclopentylresorcinol. The reader's attention is directed to Examples 1-3 were this simplified recovery is demonstrated. The hydrate of 4-cyclopentyl resorcinol will crystallize from the reaction mixture. It may be separated from the positional isomers by filtration, rather than by distillation or column chromatography, as was required by the prior art form.

C. Form I Polymorph of 4-Cyclopentyl Resorcinol

4-Cyclopentyl resorcinol monohydrate can exist as a crystalline polymorph. One crystalline polymorph has been identified to date. For simplicity, it will be referred to as the "Form I polymorph" hereinafter.

The Form I polymorph can be identified by its characteristic X-ray powder diffraction pattern. A review of FIGS. I-III shows that the Form I polymorph exhibits three characteristic peaks. A characteristic peak is one which has a significant relative intensity in the powdered XPRD pattern.

One occurs at approximately 8.1 degrees 2θ. A second occurs at approximately 23.8 degrees 2θ. A third peak occurs at approximately 16.2 degrees 2θ. Any one of these peaks alone, or in combination, may be used to identify the Form I polymorph.

In addition to these characteristic peaks, a review of FIGS. I-III shows that other minor peaks have also been identified. The intensity of these additional peaks vary with the particular orientation of the polymorph sample. These additional peaks may be used to confirm the presence of the Form I polymorph, but there absence should not be used to determine that the particular material is not the Form I polymorph. These minor peaks include: 13.9, 14.3, 18.4, 19.3, 20.1, 21.2, 25.8, and 26.54 (expressed in degrees 2θ,±0.2 °2 θ).

The structure of a single crystal of the Form I polymorph was also determined. The unit cell parameters are shown below in Table I. Table II depicts the atomic coordinates and isotropic displacement parameters. Table III depicts the hydrogen atom coordinates and isotropic displacement parameters.

TABLE I

Space Group and Unit Cell Parameters for Form I Polymorph

| Form | I |
|---|---|
| Crystal system | monoclinic |
| Space group | $P2_1/c$ |
| Cell Dimensions | |
| a(Å) | 11.313 ± 0.001 |
| b(Å) | 7.495 ± 0.001 |
| c(Å) | 12.881 ± 0.001 |
| β(°) | 110.00 ± 0.01 |
| Volume(Å$^3$) | 987 ± 1 |
| Z(Molecules/unit cell) | 4 |
| Density (g/cm$^3$) | 1.27 g/cm$^3$ |
| Temperature | 160 K |

TABLE II

Atomic Coordinates and Isotropic Displacement Parameters (Å$^2$) for 4-Cyclopentyl Resorcinol Monohydrate

| Atom | x | y | z | $U_{eq}$ |
|---|---|---|---|---|
| C1 | 0.33884(11) | 0.34881(15) | 0.46048(9) | 0.0200(3) |
| C2 | 0.37848(11) | 0.44298(16) | 0.55910(10) | 0.0218(3) |
| C3 | 0.34955(11) | 0.62334(16) | 0.55900(10) | 0.0226(3) |
| C4 | 0.28624(12) | 0.70935(16) | 0.46046(11) | 0.0267(3) |
| C5 | 0.24834(12) | 0.61175(17) | 0.36262(10) | 0.0251(3) |
| C6 | 0.27024(11) | 0.42885(16) | 0.35932(9) | 0.0206(3) |
| C7 | 0.22214(11) | 0.31688(16) | 0.25502(9) | 0.0222(3) |
| C8 | 0.15127(14) | 0.41590(19) | 0.14728(10) | 0.0323(3) |
| C9 | 0.07751(14) | 0.2711(2) | 0.06620(11) | 0.0334(3) |
| C10 | 0.07740(13) | 0.10516(19) | 0.13677(11) | 0.0312(3) |

TABLE II-continued

Atomic Coordinates and Isotropic Displacement Parameters ($Å^2$) for 4-Cyclopentyl Resorcinol Monohydrate

| Atom | x | y | z | $U_{eq}$ |
|---|---|---|---|---|
| C11 | 0.12575(13) | 0.17259(18) | 0.25632(10) | 0.0307(3) |
| O1  | 0.36575(9)  | 0.16912(11) | 0.46057(7)  | 0.0265(2) |
| O3  | 0.38290(10) | 0.71979(12) | 0.65606(8)  | 0.0301(2) |
| O12 | 0.48669(10) | 0.52361(12) | 0.84256(7)  | 0.0265(2) |

$U_{eq}$ is defined as one third of the trace of the orthogonalized $U^{ij}$ tensor

TABLE III

Hydrogen Atom Coordinates and Isotropic Displacement Parameters ($Å^2$) for 4-Cyclopentyl Resorcinol Monohydrate

| Atom | x | y | z | $U_{eq}$ |
|---|---|---|---|---|
| H2   | 0.4250     | 0.3848   | 0.6262     | 0.026 |
| H4   | 0.2689     | 0.8335   | 0.4596     | 0.032 |
| H5   | 0.2058     | 0.6721   | 0.2953     | 0.030 |
| H7   | 0.2960     | 0.2557   | 0.2450     | 0.027 |
| H8A  | 0.2110     | 0.4772   | 0.1183     | 0.039 |
| H8B  | 0.0932     | 0.5056   | 0.1597     | 0.039 |
| H9A  | 0.1187     | 0.2441   | 0.0114     | 0.040 |
| H9B  | −0.0096    | 0.3113   | 0.0263     | 0.040 |
| H10A | −0.0086    | 0.0557   | 0.1177     | 0.037 |
| H10B | 0.1335     | 0.0116   | 0.1255     | 0.037 |
| H11A | 0.1662     | 0.0752   | 0.3083     | 0.037 |
| H11B | 0.0565     | 0.2239   | 0.2774     | 0.037 |
| H1   | 0.4093(16) | 0.140(2) | 0.5238(14) | 0.032 |
| H3   | 0.4151(16) | 0.654(2) | 0.7117(14) | 0.036 |
| H12A | 0.4323(15) | 0.477(2) | 0.8658(14) | 0.032 |
| H12B | 0.5335(16) | 0.440(2) | 0.8378(13) | 0.032 |

$U_{eq}$ is defined as one third of the trace of the orthogonalized $U^{ij}$ tensor

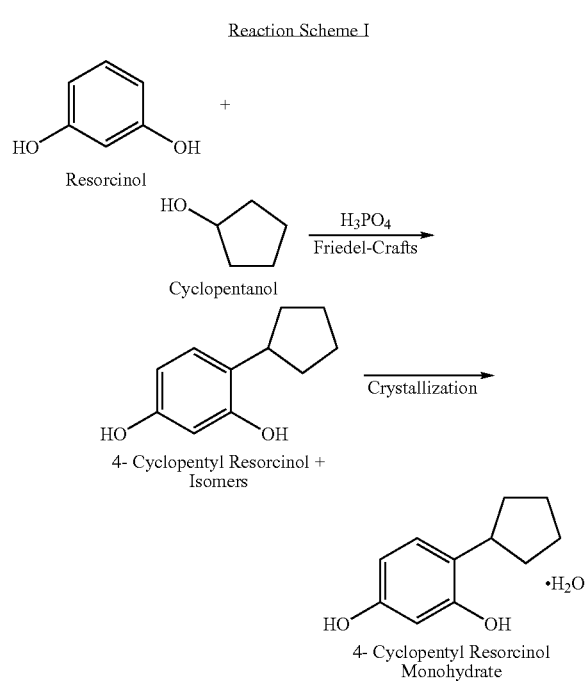

Reaction Scheme I

4-Cyclopentyl resorcinol monohydrate, and its Form I polymorph, may be prepared by methods analogously known to those skilled in the art, which are depicted in Reaction Scheme I.

The initial step is the preparation of 4-cyclopentyl resorcinol. This may be accomplished as described in U.S. Pat. No. 6,132,740, which is hereby incorporated by reference. A Friedel-Crafts reaction is carried out in which resorcinol is contacted with an excess of cyclopentanol, in the presence of a catalyst such as polyphosphoric acid, and the admixture is heated until the reaction is completed. The 4-cyclopentyl resorcinol may be recovered by extraction. Evaporation of the organic phase of the extract generates an admixture of 4-cyclopentyl resorcinol and its positional isomers.

In order to obtain the monohydrate of 4-cyclopentyl resorcinol, or its Form I polymorph, it is necessary to modify the isolation and recovery procedures described above. This may be accomplished by subjecting the anhydrate to a recrystallization, in the presence of sufficient water, using techniques analogous to those known in the art. The anhydrate is dissolved in the recrystallization solvent, cooled, and the desired monohydrate is allowed to precipitate from solution as the Form I polymorph. One suitable recrystallization solvent is an admixture of water and toluene. The ratio of toluene to water can vary widely. The Form I polymorph may be isolated by filtration, or evaporation, as is known in the art.

It has been discovered that it is not necessary to carry out separate extractions and recrystallizations. The Form I polymorph may be recovered directly by using an admixture of toluene and water as the extraction solvent. On cooling, the Form I polymorph crystallizes from solution. Likewise, other recrystallization solvents have also been utilized. The Form I polymorph has been produced from admixtures of ethanol/water, methanol/water, and isopropanol/water. The reader's attention is directed to Examples 1 to 3 where such recrystallizations are described in greater detail.

E. Pharmacology and Dose

As noted above, U.S. Pat. No. 6,132,740 describes the pharmacology of 4-cyclopentyl resorcinol. It is a tyrosinase inhibitor. It may be used to inhibit the production of melanin by melanocytes (i.e. inhibition of melanogenesis). 4-Cyclopentyl resorcinol monohydrate, and its Form I polymorph, are also tyrosinase inhibitors (hereinafter the "compounds"). They may be used in the same manner described in the '740 patent to inhibit melanogenesis. Thus, the compounds may be used to lighten areas of the skin that are inappropriately pigmented.

Examples of such inappropriate pigmentation, include solar and simple lentigines (including age/liver spots), melasma/chloasma and postinflammatory hyperpigmentation. The compounds may also be used to reduce skin melanin content in non-pathological states so as to induce a lighter skin tone, as desired by the user, or to prevent melanin accumulation in skin that has been exposed to UV irradiation. They can also be used in combination with skin peeling agents (including glycolic acid or trichloroacetic acid face peels) to lighten skin tone and prevent repigmentation.

The compounds may also be used in combination with sun screens (UVA or UVB blockers) to prevent repigmentation, to protect against sun or UV-induced skin darkening or to enhance their ability to reduce skin melanin and their skin bleaching action. The compounds used in the present invention can also be used in combination with 4-hydroxyanisole. The compounds used in this invention can also be used in combination with ascorbic acid, its derivatives and ascorbic-acid based products (such as magnesium ascorbate) or other products with an anti-oxidant mechanism (such as resveratrol) which accelerate or enhance their ability to reduce skin melanin and their skin bleaching action.

As a general guideline the compounds will be administered topically. They will be applied directly to the areas of the skin requiring depigmentation, or lightening. Topical formulations such as creams, lotions, ointments, gels, etc. will be prepared which contain from about 0.1 to 10 w/w % of the compounds. The compounds will then be applied to the affected areas from 1 to 4 times daily. If the compounds are administered systemically, then from about 0.1 mg/kg to about 100 mg/kg will be administered daily, optionally as divided doses.

F. Pharmaceutical Formulations

If desired, the compounds can be administered directly without any carrier. However, to ease administration, they will typically be formulated into pharmaceutical carriers. Likewise, they will most typically be formulated into dermatological, or cosmetic carriers. In this application the terms "dermatological carrier" and "cosmetic" carrier are being used interchangeably. They refer to formulations designed for administration directly to the skin or hair (i.e. topical formulations).

For oral administration, the compounds can be formulated into solid or liquid preparations such as capsules, pills, tablets, lozenges, melts, powders, suspensions, or emulsions. Solid unit dosage forms can be capsules of the ordinary gelatin type containing, for example, surfactants, lubricants and inert fillers such as lactose, sucrose, and cornstarch or they can be sustained release preparations.

In another embodiment, the compounds can be tableted with conventional tablet bases such as lactose, sucrose, and cornstarch in combination with binders, such as acacia, cornstarch, or gelatin, disintegrating agents such as potato starch or alginic acid, and a lubricant such as stearic acid or magnesium stearate. Liquid preparations are prepared by dissolving the active ingredient in an aqueous or non-aqueous pharmaceutically acceptable solvent, which may also contain suspending agents, sweetening agents, flavoring agents, and preservative agents as are known in the art.

For parenteral administration the compounds may be dissolved in a physiologically acceptable pharmaceutical carrier and administered as either a solution or a suspension. Illustrative of suitable pharmaceutical carriers are water, saline, dextrose solutions, fructose solutions, ethanol, or oils of animal, vegetative, or synthetic origin. The pharmaceutical carrier may also contain preservatives, buffers, etc., as are known in the art. When the compounds are being administered intrathecally, they may also be dissolved in cerebrospinal fluid as is known in the art.

Typically however, the compounds will be incorporated into formulations suitable for topical administration. Any of the topical formulations known in the art may be used. Examples of such topical formulations include lotions, sprays, creams, ointments, salves, gels, etc. Actual methods for preparing topical formulations are known or apparent to those skilled in the art, and are described in detail in Remington's Pharmaceutical Sciences, 1990 (supra); and Pharmaceutical Dosage Forms and Drug Delivery Systems, 6th ed., Williams & Wilkins (1995).

In a further embodiment, the formulations described above may be packaged for retail distribution (i.e., a kit or article of manufacture). The package will contain instructions advising the patient how to use the product in order to lighten their skin. Such instructions may be printed on the box, may be a separate leaflet or printed on the side of the container holding the formulation, etc.

G. Examples

The following examples are presented in order to further illustrate the invention. They should not be construed as limiting the invention in any manner.

EXAMPLE I

The following example describes one method for preparing 4-cyclopentyl resorcinol monohydrate, as the Form I polymorph.

A round bottom flask equipped with stirrer bar was charged with resorcinol (150 g, 1.36 moles), cyclopentanol (125 ml, 1.38 moles) and phosphoric acid (85% in water) 500 ml. The flask was fitted with a reflux condenser, purged with nitrogen and the mixture heated at 120° C. (oil bath temperature) for 26 h. After this time, TLC analysis indicated that starting resorcinol was still present. Further cyclopentanol (25 ml, 0.28 moles) was added to the reaction mixture and heating continued for 2.5 hours. On cooling, the mixture was diluted with water (500 ml) and ethyl acetate (600 ml). The organic layer was separated, and the aqueous layer extracted with ethyl acetate (3×500 ml). The combined organic layers were neutralized by careful addition of an excess of saturated aqueous sodium hydrogen carbonate solution, washed with brine (300 ml), dried (magnesium sulfate) and concentrated. The residue was dissolved in toluene (500 ml) and water (20 ml, 1.11 moles, 0.8 eq) added. The solution was stirred for ca. 30 s and cooled in an ice/water batch with periodic stirring. After 4 h the solid was filtered and left to air dry in a crystallizing dish for 16 h to give the Form I polymorph as colored crystals (118.22 g. Recrystallization in toluene afforded the Form I polymorph as white plates (93 g, 35%). Found C, 67.44, H 8.22%; $C_{11}H_{16}O_3$ requires C 67.32, H 8.22%. IR Data ($\upsilon_{max}$/cm$^{-1}$): 3199.2 br, 2963.8 s, 2863.5 s, 1624.2 m, 1604.7 s, 1528.3 s, 1457.3 s, 1395.3 s, 1349.7 w, 1287.4 m, 1265.2 s, 1228.0 s, 1179.4 m, 1166.9 m, 1108.1 s, 977.8 s, 826.5 s, 749.1 m, 723.9 m, 703.8 m and 627.9 m.

A X-ray powder diffraction pattern was generated with a sample of 4-cyclopentyl resorcinol monohydrate produced as described above. The results of this testing are depicted in FIGS. I, II and FIG. III (Lot #1).

EXAMPLE II

A single crystal of the Form I polymorph was obtained by recrystallization from isopropanol and water. The structure of this single crystal of the Form I polymorph is reported in Table I above.

EXAMPLE III

The protocol below describes an alternative method for preparing 4-cyclopentyl resorcinol monohydrate. Toluene and water are used as the extracting solvent.

To a $N_2$ purged pressure reactor is charged resorcinol (44.0 g, 0.40 mol), cyclopentanol (44 mL, 0.49 mol) and 85% aqueous $H_3PO_4$ (55 mL, 0.80 mol). The slurry is heated to 95-120° C. for 6-18 hours. The pink reaction mixture is cooled to ~70° C. and diluted with water (50 mL) and toluene (200 mL). The layers are allowed to separate at 60±5° C. The bottom orange aqueous layer is cut away. The remaining pink organic layer is extracted with 2×50 mL water at 60±5° C. and then stirred with carbon (5 g) at 60±5° C. for 1-2 hours. The slurry is filtered hot through Supercel, rinsing the cake with hot toluene (50 mL). The orange filtrate is diluted with 5 mL water and allowed to cool to ~30° C. at which time the product crystallizes. The slurry is cooled to 0-5° C. and the product collected, washed with cold toluene (40 mL) and pulled dry on the funnel to afford 41 g of 4-cyclopentyl resorcinol monohydrate as a white to pale pink solid (≧98% area by HPLC). The material can be recrystallized if desired from hot toluene (5 mL/g) and carbon (10% by weight) filtering through Supercel and/or silica gel to the Form I polymorph of 4-cyclopentyl resorcinol afford as a white solid (≧99.7% by HPLC).

The powdered X-ray diffraction pattern was determined for three (3) different lots of the Form I polymorph produced by the protocol described above. FIG. III depicts this data (Lot #'s 2-4).

EXAMPLE IV

The water content of 4-cyclopentyl resorcinol monohydrate, produced as in Example 1, was determined by Karl Fischer analysis. These analysis were conducted in the following manner:

i) Coulometric Karl Fischer (KF) Analysis

The analysis was performed using a Mettler Toledo DL39 Karl Fischer titrator. Approximately 15-20 mg of sample was placed in the KF titration vessel containing Hydranal-Coulomat AD and mixed for 10 seconds to ensure dissolution. The sample was then titrated by means of a generator electrode which produces iodine by electrochemical oxidation: $2\ I{-}{=}{>}I_2{+}2e$. Three replicates were obtained to ensure reproducibility.

ii) Volumetric Karl Fischer (KF) Analysis for Water Determination

The analysis was performed using a Mettler Toledo DL38 Karl Fischer titrator. Approximately 10-20 mg of sample was placed in the KF titration vessel containing Hydranal methanol-dry and mixed for 10 seconds to ensure dissolution. The sample was then titrated with Hydranal Composite 5 to an appropriate endpoint. Two replicates were obtained to ensure reproducibility. The titrant was standardized with Hydranal Water Standard 10.0.

The following results were obtained:

TABLE II

| Method | Run 1 % $H_2O$ | Run 2 % $H_2O$ | Run 3 % $H_2O$ | Average % $H_2O$ | Average No. mols. $H_2O$ |
|---|---|---|---|---|---|
| Volumetric | 8.95 | 9.04 | — | 9.00 | 1.08 |
| Volumetric | 9.22 | 9.80 | — | 9.51 | 1.15 |
| Coulometric | 8.12 | 8.21 | 8.58 | 8.30 | 0.99 |

The data in Table II demonstrates that Applicants have produced the monohydrate of 4-cyclopentyl resorcinol.

What is claimed is:

1. A crystalline Form I polymorph of 4-cyclopentyl resorcinol monohydrate that exhibits an X-ray powder diffraction pattern having a characteristic peak expressed in degrees 2θ at approximately 8.1.

2. A method for lightening skin comprising administering the crystalline Form according to claim 1 to a patient in need thereof.

3. A method for reducing pigmentation in skin comprising administering the crystalline Form according to claim 1 to a patient in need thereof.

4. A crystalline polymorph of 4-cyclopentyl resorcinol monohydrate that exhibits an X-ray powder diffraction pattern having a characteristic peak expressed in degrees 2θ at approximately 23.8.

5. A crystalline polymorph of 4-cyclopentyl resorcinol monohydrate that exhibits an X-ray powder diffraction pattern having characteristic peaks expressed in degrees 2θ at approximately 8.1 and 23.8.

6. The crystalline polymorph according to claim 5 that exhibits a characteristic peak expressed in degrees 2θ at approximately 16.2.

7. The crystalline polymorph according to claim 5 which exhibits at least one peak expressed in degrees 2θ at approximately 20.0 and 25.8.

8. The crystalline polymorph according to claim 5 which exhibits at least one peak expressed in degrees 2θ at approximately 13.9, 14.3, 18.4, 19.3, 20.0, 21.3, 25.8 or 26.5.

9. A crystalline polymorph of 4-cyclopentyl resorcinol monohydrate that exhibits a single crystal X-ray crystallographic analysis at 160 K with crystal unit cell parameters that are equal to the following:

TABLE I

| Space Group and Unit Cell Parameters for Form I Polymorph | |
|---|---|
| Form | I |
| Crystal system | monoclinic |
| Space group | $P2_1/c$ |
| Cell Dimensions | |
| a(Å) | 11.313 ± 0.001 |
| b(Å) | 7.495 ± 0.001 |
| c(Å) | 12.881 ± 0.001 |
| β(°) | 110.00 ± 0.01 |
| Volume(Å$^3$) | 987 ± 1 |
| Z(Molecules/unit cell) | 4 |
| Density (g/cm$^3$) | 1.27 g/cm$^3$ |
| Temperature | 160 K. |

* * * * *